United States Patent [19]

Gewartowski

[11] 4,053,367

[45] Oct. 11, 1977

[54] TEMPERATURE CONTROL OF INTEGRATED FRACTIONATION AND CLAYTREATING OF HYDROCARBONS

[75] Inventor: Steve A. Gewartowski, Mount Prospect, Ill.

[73] Assignee: UOP Inc., Des Plaines, Ill.

[21] Appl. No.: 762,220

[22] Filed: Jan. 24, 1977

Related U.S. Application Data

[63] Continuation-in-part of Ser. No. 717,978, Aug. 26, 1976, Pat. No. 4,024,026.

[51] Int. Cl.² .................. B01D 3/42; C07C 7/04; C07C 7/12
[52] U.S. Cl. .................. 203/2; 203/23; 203/41; 203/DIG. 18; 208/DIG. 1; 208/260; 260/674 SA; 260/674 R; 260/672 R; 260/672 NC; 260/668 A
[58] Field of Search ............... 203/2, 23, 41, DIG. 18; 208/DIG. 1, 260; 260/674 SA, 674 R, 672 R, 672 NC

[56] References Cited

U.S. PATENT DOCUMENTS

| 2,733,286 | 1/1956 | Maisel et al. | 260/674 R |
| 2,775,632 | 12/1956 | Honeycutt et al. | 260/674 SA |
| 3,291,850 | 12/1966 | Carson | 260/672 NC |
| 3,434,934 | 3/1969 | Washer | 203/2 |
| 3,446,709 | 5/1969 | Marshall | 196/132 |
| 3,555,837 | 1/1971 | McClintock | 196/132 |
| 3,754,045 | 8/1973 | Ehrlich et al. | 260/672 NC |
| 3,835,037 | 9/1974 | Fairweather et al. | 260/674 SE |
| 4,024,026 | 5/1977 | Gewartowski | 260/674 SA X |

*Primary Examiner*—Delbert E. Gantz
*Assistant Examiner*—C. E. Spresser
*Attorney, Agent, or Firm*—James R. Hoatson, Jr.; John F. Spears, Jr.; William H. Page, II

[57] ABSTRACT

A hydrocarbon stream comprising benzene is stripped at a high temperature to allow passage of the stripper bottoms stream into a clay treating zone without further heating, and the effluent of the clay treating zone is then exchanged against the feed stream to the stripper column to recover heat. Operation at the optimum clay treating temperature is achieved by adjusting the amount of the stripper bottoms stream which is split off for cooling by heat exchange against the feed to the stripper column. The cooled split-off portion is then admixed with the remaining high temperature portion. Adjusting the flow rate of the portion of hot clay treater effluent which is heat exchanged against the stripper feed stream is performed to control the temperature of either the stripper feed stream or the temperature of the clay treater effluent as it is passed into a downstream fractionator.

10 Claims, 1 Drawing Figure

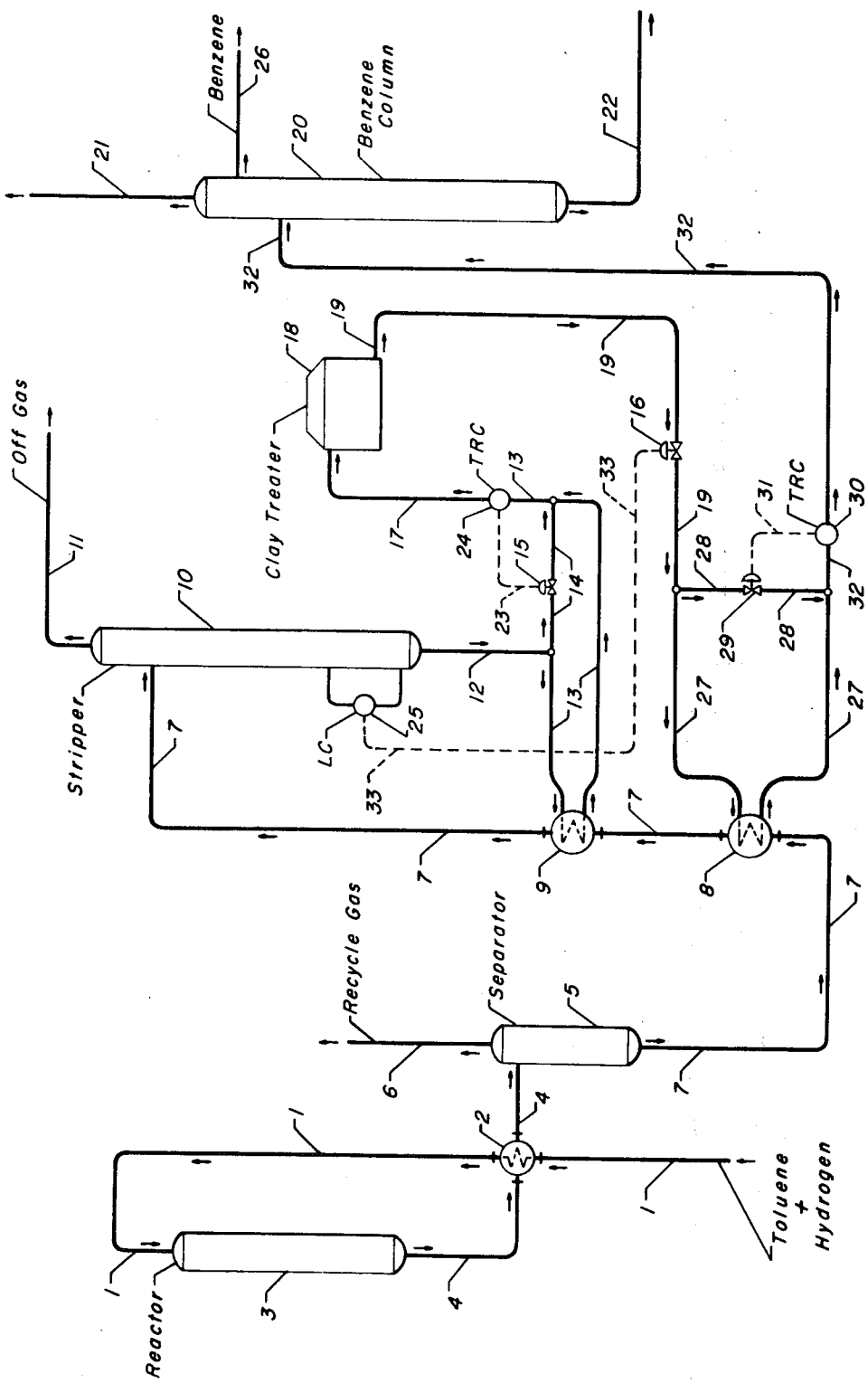

TEMPERATURE CONTROL OF INTEGRATED FRACTIONATION AND CLAYTREATING OF HYDROCARBONS

CROSS-REFERENCE TO RELATED APPLICATION

This application is a Continuation-In-Part of my copending prior application Ser. No. 717,978, filed Aug. 26, 1976, now U.S. Pat. No. 4,024,026.

FIELD OF THE INVENTION

The invention relates to a temperature control method for use on a process for the fractionation and clay treatment of hydrocarbons. The invention more specifically relates to the integration of the heat exchange used in connection with a stripping column and a downstream clay treating zone through which a stream of aromatic hydrocarbons is passed in sequence. A preferred feed stream is the condensed effluent of a hydrodealkylation zone.

PRIOR ART

The operations of fractionation and clay treatment of hydrocarbons are both well developed and are widely practiced in the petroleum and petrochemical industries. It is normally the heavier hydrocarbons, that is those having six or more carbon atoms per molecule, which are subjected to clay treating rather than lighter hydrocarbons. This segregation is often accomplished by fractional distillation. A common flow scheme therefore consists of the passage of a reaction zone effluent stream into a stripping column followed by passage of the bottoms stream of the stripping column through a clay treating zone. This is illustrated in U.S. Pat. No. 3,754,045 (Cl. 260-672NC). This reference teaches the passage of the stripping column bottoms directly into the clay treating zone and is concerned with the hydrodealkylation of toluene. The effluent of the clay treating zone is passed into a benzene column. U.S. Pat. No. 2,733,286 (Cl. 260-674) illustrates the clay treatment of a benzene-rich intermediate fraction derived from a thermally cracked heavy naphtha or gas oil. The effluent of this clay treating zone is then passed into a fractionation column used to remove the heavy polymers formed by the polymerization of olefins and diolefins in the clay treating zone.

Another of the common flow schemes utilizing distillation followed by clay treating is shown in U.S. Pat. No. 2,775,632 (Cl. 260-674). In this process a naphtha is subjected to a reforming operation and the reformate is separated by liquid-liquid extraction to produce a stream rich in aromatic hydrocarbons. This stream is dried, typically by distillation, clay treated and then distilled for the removal of polymers. The result is a nitration grade aromatic product. This reference teaches the use of a temperature of from 275° F. to 375° F. and a pressure sufficient to maintain liquid phase conditions in the clay treating zone. A similar process is described in U.S. Pat. No. 2,744,942 (Cl. 260-674). Previously cited U.S. Pat. No. 2,733,286 increases the range of suitable clay treating temperatures to 250° F. to 400° F., and U.S. Pat. No. 3,835,037 (Cl. 208-260) lowers the bottom limit of the range to about 203° F. to 257° F.

The preferred configuration of the operations upstream of the clay treating zone is shown in U.S. Pat. No. 3,285,986 (Cl. 260-674). This reference describes the treatment of the effluent of a thermal hydrodealkylation zone used to produce benzene from various alkylbenzenes. This effluent stream is first partially condensed and then separated into liquid and vapor phase portions. The liquid phase portion is passed into a stripping column which removes light hydrocarbons overhead to produce a bottoms stream of $C_6$-plus liquid. The conditions taught for use in the stripping column include a kettle temperature of about 447° F. at a pressure of about 300 psia. Previously cited U.S. Pat. No. 2,778,863 teaches operation of the column directly upstream of a clay treating zone at a pressure of about 100 psig. and a bottom temperature of 380° F. The prior art stripping-clay treating sequence is also illustrated in U.S. Pat. No. 3,291,850 (Cl. 260-672).

Other references illustrating the arts hydrocarbon separation and fractionation control are U.S. Pat. Nos. 3,434,934 (Cl. 202-154); 3,446,709 (Cl. 193-132) and 3,555,837 (Cl. 62-17).

Heretofore, the bottoms stream of the stripping column was not bifurcated into two streams, and one of these streams was not cooled and then remixed with the other to adjust the clay treater inlet temperature. In the prior art systems this bottoms stream is heated or cooled as needed as an entity.

BRIEF SUMMARY OF THE INVENTION

The invention provides a method of controlling the inlet temperature of a stream of hydrocarbons fed to a clay treating zone from the bottom of a fractionation column. The invention also provides a system for adjusting the temperature of the clay treating zone effluent stream before it is passed into the next processing step or of adjusting the temperature of the feed stream to the fractionation column. The invention also provides a system for stripping and clay treating a hydrocarbon stream which comprises a first and a second indirect heat exchange means located on the transfer line carrying the hydrocarbon stream to a stripping column, a means of bifurcating the bottoms stream of the stripping column into two portions, a first control valve means for regulating the relative flow rate of these two portions, means to direct one portion of the bottoms stream through the second heat exchange means, a commingling means to then admix the two portions of the stripping column bottoms stream, a first temperature measuring and control means which determines the temperature of the recombined bottoms stream and generates a signal representative of the difference between this temperature and the instantaneous desired inlet temperature of the clay treating zone for transmission to the first control valve means, a means of bifurcating the effluent stream of the clay treating zone effluent stream into two portions, a second control valve means for regulating the relative flow rate of these two portions, means to direct one portion of the clay treating zone effluent stream through the first heat exchange means, a commingling means to then admix the two portions of the clay treating zone effluent stream, and a second temperature measuring and control means which determines the temperature of the recombined clay treating zone effluent stream and generates a signal representative of the difference between this temperature and the instantaneous desired inlet temperature of the next processing step for transmission to the second control valve means.

One method used in conjunction with this system comprises the steps of removing a bottoms stream from the stripping column while it is operated with a bottom temperature in excess of the maximum desired inlet temperature of the clay treating zone, cooling this bottoms stream by first dividing it into two portions and cooling one portion by heat exchange against the feed stream to the stripping column and then recombining the two portions of the bottoms stream, measuring the resultant lower temperature of the bottoms stream and comparing the measured temperature to the then desired inlet temperature of the clay treating zone, and adjusting the relative flow rates of the first portion and the second portion of the bottoms stream in a manner which changes the measured temperature to the desired inlet temperature. The recombined bottoms stream is then passed into the clay treating zone, and the desired inlet temperature of the clay treating zone is gradually increased during the useful life of the clay until some maximum temperature is reached. The remaining steps in the subject method include cooling the clay treating zone effluent stream by first dividing it into two portions and cooling one portion by heat exchange against the feed stream to the stripping column and then recombining the two portions of the clay treating zone effluent stream, measuring the resultant lower temperature of the clay treating zone effluent stream and comparing the measured temperature to the then desired inlet temperature of the processing operation next downstream of the clay treating zone, and adjusting the relative flow rates of the first portion and the second portion of the clay treating zone effluent stream in a manner which changes the measured temperature to the desired inlet temperature. Other embodiments of the invention are described herein and include the division of the clay treating zone effluent stream according to the temperature of the feed stream to thereby regulate the temperature of the feed stream.

DESCRIPTION OF THE DRAWING

The drawing depicts the preferred embodiment of the invention. It is assumed that a mixture of toluene and hydrogen is charged through line 1 and heat exchanged against a reaction zone effluent stream in a feed-effluent heat exchanger 2. It is then further heated by a furnace not shown and passed through a hydrodealkylation reaction zone 3. The effluent of this reaction zone is passed through the heat exchanger 2 and into a vapor-liquid separator 5 via transfer line 4. Other cooling means not shown may be located in line 4. A hydrogen-rich recycle gas stream is removed from the separator in line 6, and a condensate stream containing benzene and toluene is removed in line 7. The condensate stream is heated in a first heat exchanger 8 and a second heat exchanger 9 and then passed into a stripping column 10. This column is operated with a bottom temperature which is maintained above the maximum desired inlet temperature of the clay treating zone 18 by a reboiler system which is not shown. An overhead stream containing essentially all of the $C_1$–$C_5$ hydrocarbons in the condensate stream and a very minor amount of benzene is removed from the stripping column in line 11.

A bottoms stream comprising benzene and toluene is removed from the stripping column in line 12 and is divided into a first portion which passes through line 14 at a rate controlled by valve 15 and a second portion which passes through line 13. The rate of flow of the bottoms stream in transfer line 12 is preferably controlled through use of a valve means 16 located downstream of clay treater 18. This valve is actuated by a signal carried by means 33 in response to a level control system 25 in the bottom of the stripping column. The second portion of the bottoms stream is cooled in the second heat exchanger 9 by exchange against the condensate stream and is then admixed with the first portion of the bottoms stream. This recombined bottoms stream is carried to the clay treater 18 by line 17. The temperature of this stream is monitored by a temperature sensor and control means 24 which generates a signal carried by means 23 to the valve 15. This signal is based on a comparison of the actual temperature of the cooled bottoms stream to the then desired clay treater inlet temperature which is performed by means 24.

The bottoms stream emerges from the clay treater as an effluent stream in line 19. This effluent stream is also divided into two portions. A first portion carried by line 27 is cooled in the first heat exchange means 8 and a second portion is passed around this heat exchange means through line 28 at a rate controlled by valve means 29. The two portions of the clay treater effluent stream are then combined and flow through a temperature sensing and control means 30 in line 32. This control means generates a signal carried to valve 29 by means 31 which is indicative of the difference between the instantaneous temperature of the recombined clay treater effluent stream and its desired temperature. Valve 29 is adjusted in response to this signal to correct the ratio of the flow rates of two portions of the clay treater effluent stream. The clay treater effluent stream is then passed into benzene column 20. This column separates the effluent stream into an overhead stream carried in line 21, a benzene sidecut stream removed through line 26 and a bottom stream comprising toluene and polymers from the clay treating operation removed in line 22.

Required subsystems and assemblies such as valves, control systems, reboilers, condensers and fractionator internals have been deleted for the purposes of simplicity and clarity. This description of one mode of the preferred embodiment is not intended to limit the scope of the invention or to limit its practice to this mode. As indicated below, various modifications to the control system, reaction system and fractionation train may be made while still retaining the operational characteristics of the invention.

DETAILED DESCRIPTION

Clay treating is used to remove impurities from hydrocarbons in a wide variety of processes in the petroleum and petrochemical industries. The materials which are beneficially affected by this operation range from lube oils and benzene to pharmaceutical products and normal paraffins. One of the most common reasons for clay treating these materials is the removal of olefinic materials, sometimes called color bodies, in order to meet various quality specifications. As used herein the term "olefinic compound" or "olefinic material" is intended to refer to both mono and diolefins. Olefinic materials may be objectionable in aromatic hydrocarbons at even very low concentrations of about a few parts per million. Their presence is readily shown by the well known acid wash color test. Removal of these olefinic materials is, for instance, necessary for the manufacture of nitration grade aromatics including benzene, toluene and xylenes. Clay treating is also used to reduce the bromine index of various hydrocarbon products. This beneficial utility of clay treating is further demonstrated by the references which were previously cited Clay treating is used herein to refer to the passage of a liquid phase hydrocarbon stream through a fixed bed of contact material which possesses the capability of polymerizing or oligomerizing olefinic compounds present in the hydrocarbon stream. Preferably the contact material is an acidic aluminosilicate. It may be either a naturally occurring material, such as bauxite or mordenite clay, or a synthetic material and may comprise alumina, silica, magnesia or zirconia or some other compound which exhibits similar properties. Several types of clay are available commercially and are suitable for use herein. Typical of these are Filtrol 24, Filtrol 25 and Filtrol 62 produced by the Filtrol Corporation, Attapulgus clay and Tonsil clay.

As previously discussed, clay treating is now conducted over a wide temperature range of from about 203° F. to about 425° F. or more. The exact temperature utilized in the clay treating zone is dependent on at least three separate factors. The first of these is the minimum temperature which is required for the contact material to function properly. This temperature is known to increase in a positive relation to the quantity of hydrocarbons which have been treated per unit mass of contact material. The minimum required temperature is therefore affected by the prior use of the clay. A second factor is the particular type of contact material which is being used. This is related to the minimum required temperature, but is an independent factor since individual contact materials exhibit differing degrees of selectivity and other properties, such as useful life, which must be taken into account. For instance, at the same level of color body removal activity two different clays may have varying degrees of catalytic activity for undesired reactions as described below. Finally, the optimum clay treating temperature will be dependent on intrinsic and extrinsic qualities of the hydrocarbon stream being treated. These qualities include the rate of flow of the hydrocarbon stream and the concentration of olefinic compounds in it. The individual hydrocarbon species which is being treated will also be a material factor. For instance, the optimum temperature for use with normal paraffins may well differ from that for use with aromatics, and individual aromatics will also differ in the maximum temperature which may be imposed. For example, relatively stable benzene can normally be subjected to higher temperatures without adverse consequences than alkylaromatics such as ethylbenzene.

The preference for specific clays and the criticality of temperature is illustrated by the following experimental results of various clay treating tests. The purpose of the tests was to compare the clays for the desired ability to polymerize olefinic compounds and for the undesired tendency to cause the transalkylation of aromatic hydrocarbons. These tests were conducted at a pressure of 500 psig., a liquid hourly space velocity of 1.0 and with upward liquid flow. The variables examined were three clay types and temperature. In one test Filtrol 24 clay was used to treat a $C_8$ aromatic fraction. This clay exhibited an excellent ability to reduce the bromine index of the aromatics from a value of 1070 to a normal value of from 3 to 7. It was found that the activity of this clay to promote transalkylation, as measured by the increase, in weight percent, of benzene and toluene, was directly related to temperature and increased from about 0.4% at 300° F. to about 2.0% at 448° F. However, in continuous operation at 425° F. the transalkylation rate decreased from about 1.8% at 46 hours to about 1.0% at about 122 hours of operation. To further investigate the transalkylation properties of this clay a feedstock containing 93.6 wt.% diethylbenzene and 0.2 wt.% triethylbenzene was also treated under these same conditions. The sum of the ethylbenzene and the triethylbenzene in the clay treater effluent was about 4.7 wt.% at about 324° F. and increased to about 26.4 wt.% at 376° F.

A similar series of tests was performed using a Tonsil clay at the same conditions. This clay also demonstrated excellent olefin removal capabilities by reducing the bromine index of the effluent to a value of about 5 or less. The extent of the accompanying transalkylation was surprisingly low however when compared to the Filtrol clay. For instance, the weight percent of benzene and toluene in the effluent due to the clay treating was below 0.1 at temperatures of 350° F. and below and reached only 0.9 at 450° F. When charging the diethylbenzene feedstock, the effluent contained about 1.4 wt.% ethylbenzene and triethylbenzene at 325° F. and a maximum of 9.7 wt.% at 376° F.

Attapulgus clay was also tested with the $C_8$ aromatic feedstock. This clay produced an effluent having a bromine index of about 59 at 325° F. and of about 47 at 425° F. Its activity for olefin removal was therefore measurably less, but these same tests indicate its activity for the undesirable transalkylation reaction was also lower. The analysis showed only a trace of benzene and toluene indicating that essentially no transalkylation occurred.

This test data indicates the importance of using the proper clay treater inlet temperature and of being able to control and adjust this temperature during the life of the clay. The probability of fluctuations in the operation of the fractionation column which is producing the stream fed to the clay treater require the use of a control system which is not dependent on the control system of the fractionation column. Furthermore, if the clay treater is operated at a higher temperature than the upstream fractionator it is necessary to heat the clay treater feed stream to this elevated temperature. This requires the use of a separate heater and heat source, an undesirable requirement. The effluent of the clay treated is often passed into a fractionation column or other processing unit which it is desired to charge a feed stream having a constant temperature. It is therefore desirable to have a system for adjusting the temperature of the clay treater effluent stream. It is therefore an objective of this invention to provide a control system and a method for controlling at a preselected temperature a hydrocarbon stream which has been removed from a fractionation column and is being passed into a clay treater. It is another objective to provide an integrated flow and temperature control system and a method for its use on the bottoms stream of a stripping column which eliminates the need to heat the bottoms stream before passage into a clay treater and which recovers heat from the clay treater effluent to minimize the reboiler duty of the stripping column. It is yet another objective to provide an integrated fractionation and clay treating method wherein the effluent of the clay treating zone is passed into a fractionation column or other downstream unit at a substantially constant temperature despite changes in the clay treating zone inlet temperature. It is another objective of the invention to provide a method of adjusting the temperature of hydrocarbon feed stream entering the upstream fractionator while simultaneously adjusting the temperature of the fractionator effluent stream which is entering the clay treating zone.

These objectives are met by the subject method, which includes operating the fractionation column at an increased pressure which requires the use of a bottoms temperature greater than the maximum clay treater inlet temperature which will be used. This high bottoms temperature is maintained constant, preferably by a control system regulating the operation of the reboiler. The next step in the method is to cool the fractionation column bottoms stream by the unique operation of bifurcating the bottoms stream and then heat exchanging one portion of it against the relatively cool material being charged into the fractionation column. The amount of this portion will vary with such changeable factors as the instantaneous preselected clay treater inlet temperature, the temperature of the feed to the fractionation column, and the temperature and flow rate of the bottoms stream itself. For instance, as the activity of the clay decreases and the preselected temperature is gradually increased to compensate, the flow rate of the cooled portion of the bottoms stream will be adjusted downward to raise the clay treater inlet temperature.

Although the fractionation column could be operated at a temperature which would not require cooling of the bottoms stream when operating the clay treater at its maximum desired inlet temperature, it is preferred that a higher temperature is maintained in the column such that some cooling of the bottoms stream is required at all times. This makes control of the temperature more stable and allows room for adjustment. Specifically, it is preferred that the bottom temperature of the column is set at least 15° F. above the maximum foreseeable desired inlet temperature for the clay treater. Furthermore, it is preferred that at all times at least 5–10 wt.% of the bottoms stream is split off for heat exchange. The maximum amount of the bottoms stream which is split off and cooled is preferably less than 50 wt.% but may be higher. In a like manner it is preferred that at all times at least 5–10 wt.% of the clay treated effluent is by-passed around the first heat exchanger as through line 28. However, the maximum amount of the clay treater effluent which is by-passed is preferably in the order of about 70 wt.%, but may be higher.

While this description is given in terms of passing a stripping column bottoms stream through a clay treater, it is not intended to limit the scope of the invention to this preferred embodiment. The subject method may be applied to other streams, such as side-cut streams, which are withdrawn at the proper temperature. It may also be applied to the bottom streams of columns not properly referred to as stripping columns. The design and other operational aspects of the fractionation column may be as is customary and established in the art.

After being cooled, the split-off portion of the bottoms stream is admixed with the uncooled portion of the bottoms stream and the temperature of the resultant stream is measured. This temperature is compared to the clay treater inlet temperature which is desired at this point in time, and the control valve which is regulating the division of the bottoms stream is then adjusted as needed to bring the measured temperature to the desired temperature. The control valve, heat exchanger, and temperature sensing and control means used for this may be any of the conventional devices known to those skilled in the art. All of the control system components are preferably utilized as shown in the drawing. That is, the rate of the bottoms stream division is preferably set by a control valve in the transfer line carrying the uncooled portion of the bottoms stream, and the rate of flow at the total bottoms stream is regulated by a level control means which signals a control valve in the transfer line carrying the total clay treating zone effluent. This control valve may be in either line 19 or line 32. Other systems may be used to practice the method of the invention. For instance, the flow rate of the total bottoms stream may be regulated by a valve means in line 12 or the temperature of the resulting admixture could be determined by temperature measurements of both portions of the bottoms stream. Other possible variations include using a temperature measured within the clay treating zone or the temperature of the clay treating zone effluent to control the cooling of the bottoms stream.

The clay treating zone may be of any type and configuration which is effective in achieving the desired degree of purification. It may utilize either upward or downward flow, with downward flow being preferred. The pressure in the clay treating zone should be sufficient to maintain liquid phase conditions. This will normally be a pressure of from about 50 to about 500 psig. or higher. Preferably the pressure is set about 50 psig. higher than the vapor pressure of the hydrocarbons at the inlet temperature of the zone. This temperature is preferably within the range of from about 210° F. to about 425° F. Clay treating may be performed over a broad range of liquid hourly space velocities. This variable is often set by the desired on-stream life of the clay and may range from 0.5 or lower to about 10. Preferred are liquid hourly space velocities of from 1.0 to 4.0 depending on the material being treated. Two separate clay treater vessels may be used on an alternating basis to provide continuous operation. The effluent of the clay treating zone is heat exchanged with the condensate stream being charged to the fractionation column. This has two beneficial results. First, it recovers a sizable amount of heat and reduces the column's reboiler duty. Second, by regulating the performance of the heat exchange as described herein the temperature of the clay treater effluent may be adjusted to a desired inlet temperature of a downstream fractionator, thus smoothing the operation of the downstream fractionator.

The invention is one of general application. That is, it may be applied to processes which differ in either their upstream or downstream configuration from that illustrated in the drawing. The upstream reaction zone may perform a different purpose, such as the catalytic reforming of a naphtha or the isomerization of alkylaromatics including xylenes, instead of vapor phase hydrodealkylation. The invention may also be utilized as part of a feed pretreatment operation which is upstream of a reaction zone. Another area of which the invention is subject to variation is the downstream or second fractionation column. This is preferably a trayed column to which the clay treater effluent stream is charged at an intermediate point. It may however be a stripping column or a packed column.

In accordance with the above description, the preferred embodiment of my invention may be characterized as a process for controlling the temperature of a stripping column bottoms stream as it is being passed into a clay treating zone and of adjusting the temperature of the clay treating zone effluent stream which comprises the steps of passing a hydrocarbon feed stream comprising $C_2$–$C_8$ hydrocarbons into a stripping column operated at effective fractionation conditions including a bottom temperature above a maximum desired inlet temperature of a downstream clay treating zone and effecting the removal of $C_2$–$C_5$ hydrocarbons from the hydrocarbon feed stream by fractionation to thereby produce a stripping column bottoms stream having a first temperature which is above an instantaneous preselected inlet temperature for the clay treating zone; cooling the stripping column bottoms stream to a second temperature by dividing the stripping column bottoms stream into a first portion and a second portion, cooling the second portion by indirect heat exchange against the hydrocarbon feed stream, and then recombining the first portion and the second portion of the stripping column bottoms stream; measuring the second temperature of the stripping column bottoms stream, and comparing the second temperature to the instantaneous preselected inlet temperature for the clay treating zone; adjusting the relative flow rates of the first portion and the second portion of the stripping column bottoms stream in a manner which changes the second temperature of the stripping column bottoms stream to the instantaneous preselected inlet temperature of the clay treating zone; passing the stripping column bottoms stream through the clay treating zone at clay treating conditions including an inlet temperature within the range of from about 210° F. to about 425° F. to produce a clay treating zone effluent stream having a first temperature; cooling the clay treating zone effluent stream to a second temperature by dividing the clay treating zone effluent stream into a first portion and a second portion, cooling the second portion by indirect heat exchange against the hydrocarbon feed stream, and then recombining the first portion and the second portion of the clay treating zone effluent stream; measuring the second temperature of the clay treating zone effluent stream, and comparing the second temperature to the instantaneous preselected inlet temperature of a downstream fractionation column; adjusting the relative flow rates of the first portion and the second portion of the clay treating zone effluent stream in a manner which changes the second temperature of the clay treating zone effluent stream to the instantaneous preselected inlet temperature of the second fractionation column and passing the clay treating zone effluent stream into an intermediate point of the downstream fractionation column.

In a different embodiment of the invention the temperature measurement and control means 30 shown in line 32 of the drawing is moved to line 7. Preferably, it is placed downstream of the second heat exchanger 9. In this embodiment the portion of the clay treater effluent stream which is passed through line 28, and therefore not cooled, is adjusted in a manner which changes the measured or actual temperature of the hydrocarbon feed stream to the then preselected inlet temperature of the stripping column 10. This may be used to compensate for changes in the amount of heat delivered to the feed stream by the relatively hot stripping column bottoms material passing through line 13. The two portions of the clay treater effluent are then recombined and fed into a downstream processing unit such as fractionator 20. It is also preferred that the sequence of heat exchange steps performed in heat exchangers 8 and 9 be in the order illustrated in the drawing. As an alternative, the hydrocarbon feed stream may be first heat exchanged with the second portion of the stripper bottoms stream and then heat exchanged with the second portion of the clay treater effluent stream.

There are two other advantages to the high temperature fractionation operation of the invention. First, the recovery of heavier components, such as benzene, in the bottoms stream of a stripping column is greater than at a lower pressure and temperature. Second, the overhead vapors of the column are at higher temperatures which allow more efficient utilization of their heat content. For instance, they can be used to generate steam or as a heating fluid for the reboiler of another column. While these two advantages to high temperature operation have been known for some time, the synergy of their benefits with those of the invention overcome the disadvantages of high temperature operation.

The preferred embodiment of the invention is further illustrated by the following example based on a catalytic dealkylation unit designed for the production of benzene from toluene and heavier aromatics. At the beginning of the run the desired inlet temperature to the clay treating zone is 350° F., and the end-of-run desired inlet temperature is 420° F. The reaction zone effluent is cooled to form a net condensate stream which is separated from the remaining vapors. This condensate stream is produced at a rate of about 4,706 BPD (barrels per day) and is depressurized to about 260 psig. to form the mixed-phase feed stream to a stripping column. This stream enters the first heat exchanger at a temperature of about 100° F. It is therein raised in temperature to about 182° F. by heat exchange against the clay treating zone effluent stream. Heat exchange in the second exchanger against a portion of the stripping column bottoms further heats this stream to about 288° F., and it is then passed into the stripping column at the top tray. The stripping column is operated with an overhead vapor temperature of 300° F. at a pressure of about 250 psig. About 34.8 moles per hour of gases are vented from the column's overhead receiver. Of this about 66 mole percent is methane, about 20 mole percent is ethane and about 12 mole percent is hydrogen. The stripping column is operated with a bottom liquid temperature of about 437° F. The net bottoms stream has a flow rate of about 4,567 BPD and is cooled to 350° F. by heat exchanging a split-off portion of it against the feed to the stripping column and described above and then recombining the portions.

Passage of the bottoms stream through the clay treating zone produces a clay treating zone effluent stream having a temperature of about 340° F. and a pressure of about 230 psig. This effluent stream is cooled to approximately 272° F. by heat exchange of one portion of the total effluent stream against the reaction zone condensate stream and the recombination of the cooled and uncooled portions in the manner previously described. It is then passed into a benzene column operated to produce an overhead vapor having a temperature of about 190° F. at a pressure of about 6 psig. A net benzene stream of about 3,379 BPD is removed as a sidecut. The net bottoms stream contains about 41 BPD of heavy aromatics which are rejected and about 1147 BPD of aromatics which are recycled to the reaction zone.

When operating at end-of-run conditions, the reaction zone condensate stream is heated to about 267° F. in the first heat exchanger by the clay treating zone effluent. Passage through the second heat exchanger again raises its temperature to about 288° F. prior to passage into the stripping column, which is operated at the same conditions. The stripping column bottoms stream is removed at the same temperature of about 437° F., but is only cooled to 420° F. by the heat exchange of a smaller portion against the condensate stream. The clay treater effluent emerges at a temperature of about 410° F., and it is then cooled by heat exchange against the condensate stream down to the benzene column feed temperature of about 272° F. The greater amount of cooling required at end-of-run conditions is achieved by passing a much larger portion of the clay treater effluent through the first heat exchanger.

I claim as my invention:

1. A method for controlling the temperature of a fractionation column effluent stream as the effluent stream is being passed into a clay treating zone and of adjusting the temperature of the clay treating zone effluent stream which comprises the steps of:
   a. passing a hydrocarbon feed stream which comprises $C_2$–$C_8$ hydrocarbons into a first fractionation column operated at effective fractionation conditions including a bottom temperature above a maximum desired inlet temperature of a downstream clay treating zone, and effecting the removal of $C_2$–$C_5$ hydrocarbons from the hydrocarbon feed stream by fractionation to thereby produce a fractionation column effluent stream having a first temperature which is above an instantaneous preselected inlet temperature for the clay treating zone;
   b. cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;
   c. measuring the second temperature of the fractionation column effluent stream, and comparing the second temperature to the instantaneous preselected inlet temperature for the clay treating zone;
   d. adjusting the relative flow rates of the first portion and the second portion of the fractionation column effluent stream in a manner which changes the second temperature of the fractionation column effluent stream to the instantaneous preselected inlet temperature for the clay treating zone;
   e. passing the fractionation column effluent stream through the clay treating zone at clay treating conditions including an inlet temperature within the range of from about 210° F. to about 425° F. to produce a clay treating zone effluent stream having a first temperature;
   f. cooling the clay treating zone effluent stream to a second temperature by dividing the clay treating zone effluent stream into a first portion and a second portion, cooling the second portion by indirect heat exchange against the hydrocarbon feed stream, and then recombining the first portion and the second portion of the clay treating zone effluent stream;
   g. measuring the second temperature of the clay treating zone effluent stream, and comparing the second temperature to the instantaneous preselected inlet temperature of a downstream second fractionation column; and,
   h. adjusting the relative flow rates of the first portion of the second portion of the clay treating zone effluent stream in a manner which changes the second temperature of the clay treating zone effluent stream to the instantaneous preselected inlet temperature of the second fractionation column.

2. The method of claim 1 wherein the fractionation column effluent stream is the bottoms stream of the first fractionation column.

3. The method of claim 2 wherein after passage through the clay treating zone the fractionation column bottoms stream is heat exchanged against the hydrocarbon feed stream to effect the heating of the hydrocarbon feed stream at a point prior to the heat exchange of step (b).

4. The method of claim 2 wherein the hydrocarbon feed stream comprises aromatic hydrocarbons.

5. The method of claim 2 wherein the hydrocarbon feed stream comprises diethylbenzene.

6. The method of claim 4 wherein the hydrocarbon feed stream is derived by the partial condensation and vapor-liquid separation of a vapor phase hydrodealkylation reaction zone effluent stream.

7. The method of claim 4 wherein the hydrocarbon feed stream is derived from an effluent stream of an alkylaromatic hydrocarbon isomerization zone and comprises paraxylene.

8. A method for controlling the temperature of a fractionation column effluent stream as the effluent stream is being passed into a clay treating zone and of adjusting the temperature of the hydrocarbon stream being fed to the fractionator column which comprises the steps of:
   a. measuring the existing temperature of a hydrocarbon feed stream which comprises $C_2$–$C_8$ hydrocarbons as the hydrocarbon feed stream is being passed into a fractionation column operated at effective fractionation conditions including a bottom temperature above a desired inlet temperature of a downstream clay treating zone, and effecting the removal of $C_2$–$C_5$ hydrocarbons from the hydrocarbon feed stream by fractionation to thereby produce a fractionation column effluent stream having a first temperature which is above an instantaneous preselected inlet temperature for the clay treating zone;
   b. cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;
   c. measuring the second temperature of the fractionation column effluent stream, and comparing the second temperature to the instantaneous preselected inlet temperature for the clay treating zone;
   d. adjusting the relative flow rates of the first portion and the second portion of the fractionation column effluent stream in a manner which changes the second temperature of the fractionation column effluent stream to the instantaneous preselected inlet temperature for the clay treating zone;
   e. passing the fractionation column effluent stream through the clay treating zone at clay treating conditions including an inlet temperature within the range of from about 210° F. to about 425° F. to produce a clay treating zone effluent stream;
   f. dividing the clay treating zone effluent stream into a first portion and a second portion, heat exchanging the second portion against the hydrocarbon feed stream and thereby heating the hydrocarbon feed stream, and then recombining the first portion and the second portion of the clay treating zone effluent stream;

g. comparing the existing temperature of the hydrocarbon feed stream to a preselected inlet temperature for the hydrocarbon feed stream; and, h. adjusting the relative flow rates of the first portion and the second portion of the clay treating zone effluent stream in a manner which changes the existing temperature of the hydrocarbon feed stream as determined in step (a) to the preselected inlet temperature of the hydrocarbon feed stream entering the fractionation column.

9. The method of claim 8 wherein the hydrocarbon feed stream is first heat exchanged against the second portion of the clay treating zone effluent stream and is then heat exchanged against the second portion of the fractionation column effluent stream.

10. The method of claim 8 wherein the hydrocarbon feed stream comprises aromatic hydrocarbons.

* * * * *